United States Patent [19]
Robert et al.

[11] Patent Number: 5,230,894
[45] Date of Patent: Jul. 27, 1993

[54] ACARICIDAL COMPOSITION SUITABLE FOR USE AGAINST VARROATOSIS IN BEES AND DEVICE CONTAINING SAME

[76] Inventors: Jean-Edouard Robert, 9/11 avenue Sainte Foy, F-92200 Neuilly sur Seine; Henri Champseix, 2 chemin de Cambas "Pioch de Baillos", F-34980 Montferrier/Lez; Joseph Maby, 9 route de Loches, F-37170 Chambray les Tours; Bernard Collin, Place Anne de Rohan, F-37800 Sainte Maure, all of France

[21] Appl. No.: 832,412

[22] Filed: Feb. 7, 1992

[30] Foreign Application Priority Data

Feb. 11, 1991 [FR] France .................. 91 01529

[51] Int. Cl.⁵ .................. A01N 25/34; A01N 37/52
[52] U.S. Cl. .................. 424/411; 424/405; 424/410; 424/84
[58] Field of Search .................. 424/405, 409, 410, 411, 424/412, 413, 84; 514/637

[56] References Cited

U.S. PATENT DOCUMENTS

| | | | |
|---|---|---|---|
| 2,073,091 | 3/1937 | Bergholm | 62/119.5 |
| 3,767,785 | 7/1969 | Bordenca et al. | 424/29 |
| 4,837,216 | 6/1989 | Mehlhorn et al. | 514/241 |

FOREIGN PATENT DOCUMENTS

| | | |
|---|---|---|
| 2073091 | 9/1971 | France . |
| 2501007 | 9/1982 | France . |
| 2638326 | 5/1990 | France . |
| 232179A | 1/1986 | German Democratic Rep. .................. 424/409 |

OTHER PUBLICATIONS

Ivanov et al. Effectiveness of Amitraz as control of Varroasis in honeybees, Chem. Abs. 107:190409p, 1987.
Chemical Abstracts, vol. 107, No. 23, 7 Dec. 1987, p. 218, 213546x.
"Compounds Which Affect the Behaviour of the Honeybee *Apis mellifera*"—Bee World 69-1988-104-123.

*Primary Examiner*—Thurman K. Page
*Attorney, Agent, or Firm*—Birch, Stewart, Kolasch & Birch

[57] ABSTRACT

The invention relates to an acaricidal composition for decontaminating bees parasitized by *Varroa jacobsoni*, and a device containing said composition suitable for installation in the hive. The composition according to the invention comprises an acaricide, a substance having properties attractive to bees and a neutral vehicle. It is applied using a semirigid support facilitating installation in the hive. The invention is applicable to the field of beekeeping.

8 Claims, No Drawings

ACARICIDAL COMPOSITION SUITABLE FOR USE AGAINST VARROATOSIS IN BEES AND DEVICE CONTAINING SAME

The present invention relates to the eradication of parasitosis in bees caused by Varroa. More particularly, the invention relates to a device containing a mixture of an acaracide and of a substance attractive to bees, as well as to the implementation of this device to decontaminate the hives.

Varroa is an acarian, which is an ectoparasite of bees. *Varroa jacobsoni* parasitizes the Asian bee *Apis cerana* in a balanced manner and without endangering the species. The introduction into Asia of the species known as *Apis mellifera* and the development of trading in swarms of bees and queens have favoured the contamination of this species by Varroa. The adaptation of *Varroa* to the *Apis mellifera* has proved lethal for the latter: a contaminated colony can be wiped out within 2 years. In the case of the *Apis mellifera* species, *Varroa* contaminates the bee right from its larval stage: the female *Varroas* establish themselves in the brood cells of the hive before the alveoli are protected by an operculum. When the alveoli are covered by an operculum, the *Varroas* reproduce on the larvae throughout their cycle of development. When the adult bee leaves the alveolus, it is parasitized by several acarians and may show signs of atrophy. The parasites pass from one bee to another in the course of social contacts between bees. The parasite can be propagated in several ways:

through the drifting of the worker bees,
through pillaging of the hives by the strongest colonies,
by the males, which may be carriers of *Varroas* and which are accepted in all the hives.

*Varroa* feeds on the haemolymph of the bee, which weakens it, reduces its activity and leads to its early death. In addition, when it feeds, the *Varroa* is capable of transmitting pathogenic viruses and microorganisms to the bee.

Varroatosis has now been propagating throughout the world for twenty years or so. Starting out from Asia, it successively reached Europe, Africa and America. In the USSR, for example, 50,000 colonies disappeared in 1971. In Europe, parasitosis is advancing at the rate of approximately 250 km per year. It was first detected in France in 1982.

This parasitosis leads to a substantial decline in the profitability of beekeeping enterprises and, moreover, poses ecological and agronomical problems owing to a reduction in the rate of pollination of the flowers in numerous varieties of plants and fruit trees.

Various treatments have already been applied:

powdering an internal zone of the hive with acaricidal products, which are disseminated by the activity of the colony;
fumigating with various repellent or acaricidal substances;
vaporizing or spraying acaricidal product based emulsions inside the hive;
placing, inside the hive, tapes of plastic material which disseminate the acaricide.

For surveillance purposes, these different methods can generally be associated with the use of an absorbent cloth, impregnated with sticky material to collect and dispose of the dead acarians, which is placed on the floor of the hive.

Selective treatments taking the form of powdering, fumigation and spraying have to be repeated regularly outside the brooding periods since the parasites present in the capped brood cells are inaccessible. In addition, the colonies can be recontaminated by visiting bees or by outside contacts with parasitized wild swarms.

Among those synthetic chemical products that are efficient as acaricides, the following deserve particular mention:

coumaphos phosphorothioic acid 0-(3-chloro-4-methyl-2-oxo-2H-1-benzopyran-7-yl)0,0-diethylester, (sold by Bayer under the name of Perizin $^M$), which is used by sprinkling the frames of the hive; the active ingredient is absorbed by the bees and is distributed throughout the colony during social food exchanges. This product can only be used in the absence of broods and outside the honey making period;

amitraz, N'-(2,4-dimethylphenyl)-N-[[(2,4-dimethyphenyl)imino]methyl]-N-methylmethanimidamide, an acaricide which is of proven efficiency against ticks and other acarians parasitizing cattle, sheep and pets, and which is also marketed for treating hives using aerosols (sold by Schering under the name of anti-varroa $^M$. This product is dangerous to the user, and it has to be carefully dosed since it can also kill the bees;

fluvalinate, N-[2-chloro-4-(trifluoromethyl)-phenyl]-DL-valine cyano(3-phenoxyphenyl)methyl ester, an acaricide with which polyvinyl chloride strips are impregnated and which slowly diffuses through the hive, thus permitting prolonged treatment (sold by Sandoz under the name of Apistan$^M$).

The evaporation of the product is dependent on climatic conditions and its efficiency thus varies. This method is particularly efficient for the purpose of decontaminating the queens and sending beekeepers cages containing the queen with a few followers.

Despite the existence of these different products, much research is still devoted to improving the methods of treatment in order to reduce the risks of toxicity for the beekeeper or the bees, as well as to guarantee that no chemical product is present in the honey or the wax.

In addition, there is always a possibility of parasites resistant to the acaracides already used making their appearance, and it is wise to continue developing alternative methods of treatment.

The present invention is based upon an original principle which aims neither to attract nor to repel the *Varroas*, but to provide an olfactory lure to attract the bees towards a device containing an acaricidal composition which acts through contact and diffusion onto the *Varroas* carried by the bees lured by a suitable attractive material contained in said composition. The quantity of acaricide can thus be reduced and localized at a precise point, more particularly in the hive, in the center of the brood comb or on a path necessarily taken by the bees that enter it. The device can remain in place for several weeks, until complete decontamination has been achieved.

As in other methods, the dead *Varroas* can be collected on an absorbent cloth placed on the floor of the hive. By regularly counting the *Varroas*, it is possible to assess the efficiency of the treatment and the degree to which the hive has been decontaminated. This method can thus be used both for surveillance and for treatment.

The present invention has been developed specifically to treat varroatosis, which is, at the present time, the most acute problem for beekeepers. It is clear that, in the event of new epidemic contamination, by another parasite, the same principle of treatment, comprising the association of a substance to lure the bees and of an antiparisitic substance would simply constitute a variant of the present invention.

Lures for bees have already been analyzed and described; particular attention is devoted to them with a view to favouring pollination and the colonization of hives at the time of swarming.

One lure that has proved particularly efficient for colonizing hives is an artificial mixture of three constituents of the pheromones secreted by the Nasonov glands of worker bees: citral, geraniol and nerolic acid in solution in hexane, used in a dose corresponding to the amount secreted by 5000 worker bees.

A smaller dose of this mixture has been incorporated in the acaricidal composition according to the present invention to attract the bees of the colony towards the device containing this composition.

More particularly, use is made of a mixture, in equal proportions, of citral and of geraniol, the mixture being added to the other constituents in a proportion representing 0.05% to 0.2% in dry weight of the final mixture. Other active substances could also be incorporated in this composition, such as geranic acid, farnesol, the constituents of royal jelly such as adipic acid, pinelic acid, suberic acid and hydroxy-4 benzoic acid. (See article entitled "Compounds which affect the behaviour of the honeybee *Apis mellifera*—Bee world 69-1988-104-123).

The acaricide used in the mixture according to the present invention is preferably amitraz, in a concentration not exceeding 10% in dry weight of the final mixture. Amitraz can be of commercial origin or prepared according to the method disclosed in French patent 2 073 091.

Another acaricides could be used in an equivalent way.

The substance with bee luring properties and the acaricide are incorporated in a neutral vehicle. According to a preferred form of embodiment of the invention, this neutral vehicle is a purified powder of polyvinylpolypyrrolidone polymer (PVPP).

The active ingredients are incorporated in the mass of the polymer by stirring at a high temperature (60° to 80° C.) in a final ratio of 0.05 to 0.02% of lure, 5 to 10% of amitraz and 90 to 95% of PVPP, the percentages being expressed in terms of dry weight.

In order to be used in the hives, the acaricidal composition according to the invention, which takes the form of a powder and may be used in an amount between 1.5 and 15 grams dry weight, has to be incorporated in a device that prevents it from being dispersed in the hive and, in particular, in the honey.

According to one form of embodiment of the invention, this device is a sachet of microporous material permitting the diffusion of the active ingredients.

According to one particular form of embodiment, the sachet is made of polyethylene, and after filling and heat sealing, it is subjected to heating, preferably at 80° C. for 4 hours, to favour impregnation of the polyethylene by the active ingredients and thus increase the efficiency of acaricidal action by direct contact with the bees.

According to another form of embodiment of the invention, the device is a sheet of polymerized polysorbate in which the acaricidal composition has been incorporated in the course of polymerization, this device also promoting direct contact between the bees and the acaricide.

According to one preferred form of embodiment of the invention, this polymerized polysorbate containing the acaricide-lure composition is moulded about a mesh like strip of semi-rigid plastic material which serves to support and hold it inside the hive, and improves its resistance to destruction by the bees.

The mesh like strip is impregnated with polysorbate and active composition only in its central portion, the upper portion being used to fasten it to the upper shelves of the hive, and the lower portion enabling the device to be unfastened simply by pulling, without opening the hive.

The present invention also relates to the implementation of the device containing the composition described for decontaminating the hives parasitized by *Varroa jacobsoni*. More particularly, the invention relates to the installation of the device inside the hive, in a place through which the worker bees necessarily pass. The device designed for hive decontamination contains a quantity of the lure-acaricide-neutral vehicle composition amounting to between 1.5 and 15 grams.

The following examples serve to illustrate the invention without limiting its scope.

EXAMPLE 1

A commercial preparation of PVPP is repurified
- by three successive treatments involving contacting with two volumes of boiling water, filtration and drying;
- by washing with boiling ethanol to remove the residual traces of water;
- by drying under vacuum (1 mm of mercury) at 100° C. for at least 2 hours.

After the temperature has been lowered to between 80° and 60° C. and the vacuum valve has been closed, the active ingredients, previously dissolved in alcohol, are incorporated in the mass of the polymer, without any air being allowed to enter the recipient, in the following proportions, expressed as percentages of the total weight:

amitraz: 5% lure (including citral and geraniol in the proportion of 1:1): 0.05%

The bee luring substances are of commercial origin (Merck Index Nos. 2293 and 4263).

The mixture is maintained at 80° C. with continuous stirring for 8 hours, and then the temperature is restored to normal and pre-dehumidified air is introduced into the recipient.

The powder thus obtained will be formulated according to the chosen mode of use, as described in the following examples (2 to 4).

EXAMPLE 2

The powder obtained using the process described in example 1 is packaged in low density polyethylene sachets or in sachets of microporous woven or nonwoven material.

1.5 to 15 grams or powder are dispensed per sachet.

EXAMPLE 3

To favour contact between the bees and the acaricide, the polyethylene sachets, each filled with 15 grams of powder, are heat sealed and then heated at 80° C. for 4 hours, to promote the diffusion of the acaracide through the polyethylene.

EXAMPLE 4

The powder obtained using the process described in example 1 is incorporated in polysorbate, a non-toxic, cold polymerizable substance, which forms a sheet that is sufficiently strong to resist destruction by the bees.

The polysorbate solution includes:

| | |
|---|---|
| demineralized water | 68% |
| polyvinyl alcohol | 10% |
| polysorbate | 2% |
| absolute ethanol | 20% |

The polyvinyl alcohol is dissolved in the water at 70° C. with mechanical stirring. Then the temperature is lowered to 30° C. for the purpose of adding the polysorbate and the ethanol.

15 g of powder obtained using the process described in example 1 are then incorporated in 85 g of polysorbate solution; when the solution is homogenous, it is spread over a silicone-coated tray so as to form a 2 mm thick layer. Polymerization is completed after 4 days. White, granulous, flexible elastic sheets are obtained. The material obtained is then cut into small strips the size of which is determined according to the dose of amitraz chosen for the treatment of one hive.

EXAMPLE 5

A mechanical device is used to render rigid or "reinforce" the strips described in Example 4. Use is made of a fine mesh of semirigid plastic material (such as "food quality" polyethylene, of commercial origin) fulfilling the following criteria:

- semirigid to facilitate its introduction into, and removal from, the hive;
- memorizing a system of folding designed to facilitate its fixing in the shelves;
- favouring the adhesion and cohesion of the polymer containing the active composition, to prevent it from being torn or peeled off by the bees.

Thus, from a material having a 5 mm square mesh are cut strips of 420 mm long by 15 mm wide, these dimensions being compatible with all the models of hive currently available. The active composition incorporated in the polysorbate is placed for polymerization only around the central portion of the strip, over a length of 150 mm, i.e. leaving, on one side, 60 mm and, on the other side, 210 mm of mesh material untreated with active substance.

Thus, whatever the format of the hive, the portion impregnated with active composition will be placed at the level of the lower two thirds of the frames, and the untreated upper portion will be fastened between the upper shelves and adapted, by means of appropriate folds, to fit the thickness of the shelves and the size of the hive. These manipulations ensure that the beekeeper is protected from any contact with the active substance. The non-impregnated zone, which is 60 mm long, and which projects from the lower portion of the frame of the hive, enables the device to be withdrawn from the hive once the treatment is completed, without any need to open the hive, simply by hooking it out through the bees' exit slit, in the area of the flight platform.

Thanks to the ease of manipulation due to the semirigid nature of this device, it is possible to save considerable time both when installing and when unfastening it. This is particularly important in the case of treatments conducted in cold weather as a drop in temperature to 10° C. can kill an entire brood.

The time saving, in the case of undertakings that can comprise as many as 4000 hives, is thus an appreciable advantage.

EXAMPLE 6

The different methods of formulation described in examples 2 to 5 are controlled:

for the quantity of active ingredients present;

for the stability of the active ingredients over time.

a) The quantities of acaricide and lure are monitored using high performance liquid chromatography after extraction with an organic solvent (absolute ethanol or acetone), by reference to control samples freshly prepared and dosed;

b) Kinetic measurements of the disappearance of the active ingredients using same dosage as in a) are conducted on the different formulations maintained under temperature and humidity conditions reproducing those of the hive, i.e. a recipient thermostatically controlled at 32° C. and having 90% relative humidity. After 6 weeks, there remains over 70% of the initial concentration of the different constituents.

EXAMPLE 7

The efficiency and innocuousness of the method of treatment are evaluated in contaminated hives.

a) Efficiency.

The device is placed in the hive, within the brood cells.

To measure the efficiency of the treatment, using the conventional method, an absorbent cloth impregnated with sticky material is placed on the floor of the hive to collect the dead Varroas, which are counted as time elapses.

One can consider that the treatment has resulted in the total elimination of the parasites when no more Varroas are collected for 3 days. This total decontamination is reached in less than 30 days.

The following table illustrates the mortality of Varroas in 20 hives monitored for 24 days. Day 0 corresponds to the installation of the strip impregnated with the active composition described in Example 5.

See table on following page

TABLE

| Days | Hive No | | | | | | | | | |
|---|---|---|---|---|---|---|---|---|---|---|
| | 1 | 2 | 3 | 4 | 5 | 6 | 7 | 8 | 9 | 10 |
| −3 | 0 | 1 | 3 | 0 | 0 | 4 | 0 | 1 | 3 | 0 |
| −2 | 1 | 2 | 2 | 1 | 12 | 1 | 1 | 2 | 2 | 1 |
| −1 | 6 | 8 | 1 | 0 | 0 | 17 | 6 | 8 | 1 | 0 |
| 0 | 0 | 0 | 0 | 0 | 0 | 0 | 0 | 0 | 0 | 0 |
| 1 | 905 | 1756 | 565 | 312 | 480 | 2130 | 680 | 1860 | 765 | 389 |

TABLE-continued

| Days | | | | | | | | | | |
|---|---|---|---|---|---|---|---|---|---|---|
| 2 | 156 | 287 | 119 | 87 | 18 | 108 | 103 | 207 | 89 | 56 |
| 3 | 67 | 65 | 54 | 17 | 17 | 12 | 48 | 61 | 52 | 19 |
| 4 | 29 | 27 | 18 | 4 | 5 | 28 | 31 | 23 | 15 | 6 |
| 5 | 14 | 101 | 13 | 12 | 0 | 3 | 14 | 113 | 16 | 13 |
| 6 | 2 | 7 | 5 | 2 | 2 | 17 | 1 | 9 | 3 | 4 |
| 7 | 9 | 23 | 2 | 5 | 3 | 10 | 11 | 25 | 4 | 2 |
| 8 | 0 | 11 | 1 | 2 | 0 | 1 | 1 | 9 | 2 | 1 |
| 9 | 0 | 22 | 3 | 8 | 0 | 4 | 0 | 22 | 3 | 8 |
| 10 | 0 | 9 | 0 | 3 | 0 | 2 | 0 | 10 | 0 | 3 |
| 11 | 0 | 15 | 0 | 3 | 0 | 81 | 0 | 25 | 0 | 3 |
| 12 | 0 | 21 | 0 | 1 | 0 | 62 | 0 | 21 | 0 | 1 |
| 13 | 0 | 27 | 0 | 3 | 4 | 29 | 0 | 23 | 0 | 2 |
| 14 | 0 | 22 | 0 | 6 | 21 | 8 | 0 | 24 | 0 | 6 |
| 15 | 0 | 5 | 0 | 0 | 5 | 14 | 0 | 5 | 0 | 0 |
| 16 | 0 | 3 | 0 | 0 | 1 | 17 | 0 | 3 | 0 | 0 |
| 17 | 0 | 3 | 0 | 0 | 13 | 0 | 0 | 3 | 0 | 0 |
| 18 | 0 | 2 | 0 | 0 | 3 | 0 | 0 | 2 | 0 | 0 |
| 19 | 0 | 0 | 0 | 0 | 0 | 0 | 0 | 0 | 0 | 0 |
| 20 | 0 | 0 | 0 | 0 | 0 | 0 | 0 | 0 | 0 | 0 |
| 21 | 0 | 0 | 0 | 0 | 0 | 0 | 0 | 0 | 0 | 0 |
| 22 | 0 | 0 | 0 | 0 | 0 | 1 | 0 | 0 | 0 | 0 |
| 23 | 0 | 0 | 0 | 0 | 0 | 0 | 0 | 0 | 0 | 0 |
| 24 | 0 | 0 | 0 | 0 | 0 | 0 | 0 | 0 | 0 | 0 |

| Days | Hive No 11 | 12 | 13 | 14 | 15 | 16 | 17 | 18 | 19 | 20 | TOTAL |
|---|---|---|---|---|---|---|---|---|---|---|---|
| −3 | 2 | 15 | 5 | 10 | 3 | 0 | 0 | 4 | 0 | 4 | 55 |
| −2 | 12 | 22 | 3 | 2 | 2 | 1 | 12 | 1 | 12 | 1 | 93 |
| −1 | 0 | 17 | 12 | 9 | 3 | 1 | 1 | 17 | 0 | 17 | 124 |
| 0 | 0 | 0 | 0 | 0 | 0 | 0 | 0 | 0 | 0 | 0 | 0 |
| 1 | 467 | 3150 | 1225 | 1789 | 899 | 423 | 789 | 2320 | 762 | 3245 | 24911 |
| 2 | 18 | 123 | 190 | 234 | 109 | 86 | 22 | 68 | 15 | 145 | 2240 |
| 3 | 18 | 29 | 120 | 58 | 22 | 19 | 12 | 11 | 17 | 12 | 730 |
| 4 | 7 | 12 | 41 | 28 | 19 | 16 | 9 | 26 | 3 | 24 | 371 |
| 5 | 0 | 6 | 17 | 68 | 16 | 12 | 0 | 3 | 0 | 3 | 424 |
| 6 | 5 | 41 | 6 | 8 | 10 | 1 | 0 | 15 | 1 | 17 | 156 |
| 7 | 3 | 9 | 13 | 22 | 5 | 6 | 4 | 5 | 2 | 8 | 171 |
| 8 | 0 | 1 | 1 | 11 | 1 | 2 | 0 | 2 | 0 | 1 | 47 |
| 9 | 0 | 4 | 2 | 5 | 3 | 8 | 0 | 4 | 0 | 4 | 100 |
| 10 | 0 | 5 | 0 | 5 | 1 | 3 | 0 | 2 | 0 | 2 | 45 |
| 11 | 0 | 112 | 0 | 34 | 1 | 7 | 0 | 101 | 0 | 132 | 514 |
| 12 | 0 | 84 | 0 | 23 | 0 | 5 | 0 | 73 | 0 | 60 | 351 |
| 13 | 5 | 29 | 0 | 30 | 0 | 4 | 4 | 24 | 14 | 45 | 243 |
| 14 | 18 | 7 | 0 | 24 | 0 | 6 | 17 | 8 | 25 | 9 | 201 |
| 15 | 3 | 13 | 0 | 5 | 0 | 0 | 3 | 19 | 13 | 11 | 96 |
| 16 | 0 | 12 | 0 | 3 | 0 | 0 | 0 | 17 | 1 | 17 | 74 |
| 17 | 0 | 6 | 0 | 3 | 0 | 0 | 0 | 2 | 5 | 3 | 38 |
| 18 | 1 | 0 | 0 | 2 | 0 | 0 | 0 | 0 | 3 | 1 | 14 |
| 19 | 0 | 0 | 0 | 0 | 0 | 0 | 1 | 0 | 0 | 0 | 1 |
| 20 | 0 | 0 | 0 | 0 | 0 | 0 | 0 | 0 | 0 | 0 | 0 |
| 21 | 0 | 0 | 0 | 0 | 0 | 0 | 0 | 0 | 0 | 0 | 0 |
| 22 | 0 | 1 | 0 | 0 | 0 | 0 | 0 | 0 | 0 | 0 | 2 |
| 23 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | b) Innocuousness

In the preliminary tests, several doses of amitraz were tested and an overdose led to the death of several colonies.

With the dose selected, i.e. one not exceeding 750 mg per package intended for one hive, no abnormal mortality of the bees is observed and no changes are noted in their activity or their behaviour;

In a control test, a dose of loose powder (neither placed in a sachet nor incorporated in a solid polymer) was distributed through the hive; even under these conditions, no bee mortality was observed.

We claim:

1. A device for treating varroa by applying an acaricidal composition to bees by direct contact with the bees, without danger to the bees or contamination of wax or honey in a beehive, comprising:
   (1) between 1.5 and 15 g dry weight of amitraz composition comprising an acaricide, a mixture of citral and geraniol in an amount attractive to bees, and a neutral carrier; and
   (2) a support or container for said acaricidal composition, capable of being placed inside a beehive, comprising a sachet made of microporous material.

2. The device according to claim 1, wherein said microporous material is a polyethylene.

3. The device according to claim 2, wherein said device is prepared by filling said polyethylene sachet with said acaricidal composition, heat sealing said filled sachet, and heating said heat sealed sachet to impregnate said polyethylene with said acaricidal composition.

4. The device according to claim 1, wherein said neutral carrier is a purified powder of polyvinylpolypyrrolidone polymer.

5. A device for between 1.5 and 15 g dry weight of treating varroa by applying an acaricidal composition to bees by direct contact with the bees, without danger to the bees or contamination of wax or honey in a beehive, comprising:
   (1) amitraz composition comprising an acaricide, a mixture of citral and geraniol in an amount attractive to bees, and a neutral carrier; and (2) a support or container for said acaricidal composition, capable of being placed inside a beehive, comprising a sheet of polymerized polysorbate.

6. The device according to claim 5, wherein said sheet of polymerized polysorbate is molded around a mesh strip of semirigid plastic material, having two ends and a central zone.

7. The device according to claim 6, wherein said sheet of polymerized polysorbate is impregnated with said acaricidal composition only in the portion molded around said central zone of said mesh strip, and wherein said two ends of said mesh strip serve to fasten and remove said device from a beehive.

8. The device according to claim 5, wherein said neutral carrier is a purified powder of polyvinylpolypyrrolidone polymer.

* * * * *